(12) United States Patent
Faries, Jr. et al.

(10) Patent No.: US 8,444,599 B2
(45) Date of Patent: May 21, 2013

(54) METHOD AND APPARATUS TO INDICATE PRIOR USE OF A MEDICAL ITEM

(75) Inventors: Durward I. Faries, Jr., Las Vegas, NV (US); Bruce R. Heymann, Vienna, VA (US); David Hendrix, Ashburn, VA (US); John Gordon, Herndon, VA (US)

(73) Assignee: Patented Medical Solutions, LLC, Las Vegas, NV (US)

( * ) Notice: Subject to any disclaimer, the term of this patent is extended or adjusted under 35 U.S.C. 154(b) by 123 days.

(21) Appl. No.: 12/776,654

(22) Filed: May 10, 2010

(65) Prior Publication Data

US 2010/0222763 A1    Sep. 2, 2010

Related U.S. Application Data

(62) Division of application No. 11/581,795, filed on Oct. 17, 2006, now Pat. No. 7,740,611.

(60) Provisional application No. 60/730,361, filed on Oct. 27, 2005.

(51) Int. Cl.
*A61M 5/00* (2006.01)
(52) U.S. Cl.
USPC .......................................... 604/111; 604/404
(58) Field of Classification Search
USPC ................ 604/97.01, 100.01, 408, 111, 404
See application file for complete search history.

(56) References Cited

U.S. PATENT DOCUMENTS

| | | | |
|---|---|---|---|
| 522,866 A | 7/1894 | Weinhagen et al. | |
| 558,979 A | 4/1896 | Noble | |
| 675,647 A | 6/1901 | Andersen et al. | |
| 785,524 A | 3/1905 | Shea | |
| 803,352 A | 10/1905 | Meyer | |
| 1,062,111 A | 5/1913 | Nylander | |
| 1,092,643 A | 4/1914 | Goolsby | |
| 1,110,919 A | 9/1914 | Gamble | |

(Continued)

FOREIGN PATENT DOCUMENTS

| | | |
|---|---|---|
| DE | 3709122 | 9/1988 |
| FR | 2711393 | 4/1995 |

(Continued)

OTHER PUBLICATIONS

"Needless Access Connector (Retrograde Free)" NAC Plus; Kipp Med; 1 page.

(Continued)

*Primary Examiner* — Nicholas Lucchesi
*Assistant Examiner* — Gerald Landry, II
(74) *Attorney, Agent, or Firm* — Edell, Shapiro & Finnan, LLC (57) ABSTRACT

The present invention monitors an IV bag injection port and informs the user of prior injections. The present invention employs an object and/or a sealed chamber within a transparent IV fluid bag injection port. In the case of the object, notification of prior use is achieved when the object's or IV fluid's appearance is altered. With respect to the sealed chamber, the chamber's seal is breached to allow fluid to pass between the chamber and the IV bag to change the appearance of the contents of the chamber. Since the injection port and bag walls are at least partially transparent, medical personnel are able to observe the altered appearance of either the object, IV fluid or the sealed chamber.

10 Claims, 7 Drawing Sheets

U.S. PATENT DOCUMENTS

| | | | |
|---|---|---|---|
| 1,223,274 A | 4/1917 | Hallock | |
| 1,390,500 A | 9/1921 | Christian | |
| 1,479,451 A | 1/1924 | Buckstein | |
| 1,493,450 A | 5/1924 | Richardson | |
| 1,726,212 A | 8/1929 | Bucky | |
| 1,770,832 A | 7/1930 | Bass | |
| 1,794,215 A | 2/1931 | Titus | |
| 1,838,026 A | 12/1931 | Williams | |
| 1,847,954 A | 3/1932 | Fisher | |
| 1,960,417 A | 5/1934 | Pain, Jr. | |
| 1,982,213 A | 11/1934 | Hopkins | |
| 1,987,119 A | 1/1935 | Long | |
| 1,995,302 A | 3/1935 | Goldstein | |
| 2,063,902 A | 12/1936 | Beasley | |
| 2,087,586 A | 7/1937 | Tishman | |
| 2,124,293 A | 7/1938 | Goldstein | |
| 2,204,764 A | 6/1940 | Mayo | |
| 2,254,994 A | 9/1941 | Butland | |
| 2,357,692 A | 9/1944 | Saffady | |
| 2,470,481 A | 5/1949 | Freeman | |
| 2,701,789 A | 2/1955 | White | |
| 2,766,907 A | 10/1956 | Wallace, Jr. | |
| 2,880,764 A | 4/1959 | Pelavin | |
| 2,910,981 A | 11/1959 | Wilson et al. | |
| 2,990,875 A | 7/1961 | Samuels et al. | |
| 3,140,716 A | 7/1964 | Harrison et al. | |
| 3,157,727 A | 11/1964 | Hardy et al. | |
| 3,247,851 A | 4/1966 | Seibert | |
| 3,293,868 A | 12/1966 | Gonzalez | |
| 3,370,153 A | 2/1968 | Du Fresne et al. | |
| 3,475,590 A | 10/1969 | Pins | |
| 3,485,245 A | 12/1969 | Lahr et al. | |
| 3,500,366 A | 3/1970 | Chesney et al. | |
| 3,526,134 A | 9/1970 | Schaus | |
| 3,551,641 A | 12/1970 | Truhan | |
| 3,563,090 A | 2/1971 | Deltour | |
| 3,590,215 A | 6/1971 | Anderson et al. | |
| 3,591,290 A | 7/1971 | Zinner et al. | |
| 3,596,515 A | 8/1971 | Cramer | |
| 3,612,059 A | 10/1971 | Ersek | |
| 3,614,385 A | 10/1971 | Horstmann | |
| 3,629,552 A | 12/1971 | Edging | |
| 3,636,767 A | 1/1972 | Duffy | |
| 3,640,277 A | 2/1972 | Adelberg | |
| 3,651,695 A | 3/1972 | Brown | |
| 3,845,661 A | 11/1974 | Hollweck et al. | |
| 3,864,976 A | 2/1975 | Parker | |
| 3,895,741 A | 7/1975 | Nugent | |
| 3,908,652 A | 9/1975 | Weissinger | |
| 3,940,742 A | 2/1976 | Hudspeth et al. | |
| 4,009,615 A | 3/1977 | Ruhl | |
| 4,038,519 A | 7/1977 | Foucras | |
| 4,063,551 A | 12/1977 | Sweeney | |
| 4,090,514 A | 5/1978 | Hinck et al. | |
| 4,098,123 A | 7/1978 | Granzow, Jr. | |
| 4,121,574 A | 10/1978 | Lester | |
| 4,121,585 A | 10/1978 | Becker, Jr. | |
| 4,138,890 A | 2/1979 | Brown | |
| 4,167,663 A | 9/1979 | Branzow, Jr. et al. | |
| 4,187,847 A | 2/1980 | Loeser | |
| 4,293,762 A | 10/1981 | Ogawa | |
| 4,309,592 A | 1/1982 | LeBoeuf | |
| 4,314,484 A | 2/1982 | Bowman | |
| 4,329,569 A | 5/1982 | Hjortsberg et al. | |
| 4,336,435 A | 6/1982 | Kashyap et al. | |
| 4,356,383 A | 10/1982 | Dahlberg | |
| 4,375,813 A | 3/1983 | Hessel | |
| 4,384,578 A | 5/1983 | Winkler | |
| 4,397,648 A | 8/1983 | Knute | |
| 4,430,077 A * | 2/1984 | Mittleman et al. | 604/111 |
| 4,430,078 A | 2/1984 | Sprague | |
| 4,432,761 A | 2/1984 | Dawe | |
| 4,464,563 A | 8/1984 | Jewett | |
| 4,476,877 A | 10/1984 | Barker | |
| 4,490,884 A | 1/1985 | Vickers | |
| 4,495,402 A | 1/1985 | Burdick et al. | |
| 4,498,901 A | 2/1985 | Finch | |
| 4,509,943 A | 4/1985 | Ilanzawa | |
| 4,522,308 A * | 6/1985 | Sullivan | 215/253 |
| 4,523,078 A | 6/1985 | Lehmann | |
| 4,529,309 A | 7/1985 | Pettersson et al. | |
| 4,531,941 A | 7/1985 | Zasuwa | |
| 4,532,414 A | 7/1985 | Shah et al. | |
| 4,533,350 A | 8/1985 | Danby et al. | |
| 4,543,095 A | 9/1985 | Jensen | |
| 4,551,136 A | 11/1985 | Mandl | |
| 4,552,277 A * | 11/1985 | Richardson et al. | 215/249 |
| 4,572,536 A | 2/1986 | Doughty | |
| 4,585,435 A | 4/1986 | Vaillancourt | |
| 4,585,441 A | 4/1986 | Archibald | |
| 4,586,691 A | 5/1986 | Kozlow | |
| 4,613,327 A | 9/1986 | Tegrarian et al. | |
| 4,614,514 A | 9/1986 | Carr et al. | |
| 4,625,086 A | 11/1986 | Karino | |
| 4,626,243 A | 12/1986 | Singh et al. | |
| 4,628,186 A | 12/1986 | Bergemann et al. | |
| 4,634,432 A | 1/1987 | Kocak | |
| 4,647,756 A | 3/1987 | Willis | |
| 4,651,813 A | 3/1987 | Witt et al. | |
| 4,657,004 A | 4/1987 | Coffey | |
| 4,673,820 A | 6/1987 | Kamen | |
| 4,674,977 A | 6/1987 | Hoselton | |
| 4,678,460 A | 7/1987 | Rosner | |
| 4,680,445 A | 7/1987 | Ogawa | |
| 4,680,977 A | 7/1987 | Conero et al. | |
| 4,682,979 A | 7/1987 | Girouard | |
| 4,684,367 A | 8/1987 | Schaffer et al. | |
| 4,705,505 A | 11/1987 | Fried | |
| 4,707,587 A | 11/1987 | Greenblatt | |
| 4,709,135 A | 11/1987 | Dietrich et al. | |
| 4,718,896 A | 1/1988 | Arndt et al. | |
| 4,735,609 A | 4/1988 | Comeau et al. | |
| 4,745,248 A | 5/1988 | Hayes | |
| 4,747,450 A | 5/1988 | Ikegame et al. | |
| 4,747,826 A | 5/1988 | Sassano | |
| 4,756,299 A | 7/1988 | Podella | |
| 4,759,749 A | 7/1988 | Verkaart | |
| 4,772,778 A | 9/1988 | Ogawa | |
| 4,781,548 A | 11/1988 | Alderson et al. | |
| 4,782,212 A | 11/1988 | Bakke | |
| 4,801,777 A | 1/1989 | Auerbach | |
| 4,804,367 A | 2/1989 | Smith et al. | |
| 4,808,159 A | 2/1989 | Wilson | |
| 4,823,833 A | 4/1989 | Hogan et al. | |
| 4,832,689 A | 5/1989 | Mauerer et al. | |
| 4,844,074 A | 7/1989 | Kurucz | |
| 4,844,397 A | 7/1989 | Skakoon et al. | |
| 4,847,470 A | 7/1989 | Bakke | |
| 4,859,360 A | 8/1989 | Suzuki et al. | |
| 4,874,033 A | 10/1989 | Chatelain et al. | |
| 4,874,359 A | 10/1989 | White et al. | |
| 4,878,537 A | 11/1989 | Verkaart | |
| 4,878,588 A | 11/1989 | Ephraim | |
| 4,900,308 A | 2/1990 | Verkaart | |
| 4,904,848 A | 2/1990 | Colevas | |
| 4,906,816 A | 3/1990 | van Leerdam | |
| 4,923,681 A | 5/1990 | Cox et al. | |
| 4,934,152 A | 6/1990 | Templeton | |
| 4,934,336 A | 6/1990 | White | |
| 4,936,828 A | 6/1990 | Chiang | |
| 4,991,976 A | 2/1991 | Byles | |
| 5,013,889 A | 5/1991 | Bakke | |
| 5,019,047 A | 5/1991 | Kriesel | |
| 5,040,380 A | 8/1991 | Gregory | |
| 5,040,699 A | 8/1991 | Gangemi | |
| 5,042,455 A | 8/1991 | Yue et al. | |
| 5,059,182 A | 10/1991 | Laing | |
| 5,061,241 A | 10/1991 | Stephens, Jr. et al. | |
| 5,061,630 A | 10/1991 | Knopf et al. | |
| 5,063,994 A | 11/1991 | Verkaart | |
| 5,073,167 A | 12/1991 | Carr et al. | |
| 5,074,658 A | 12/1991 | Tavlarides et al. | |
| 5,075,167 A | 12/1991 | Yamauchi et al. | |
| 5,081,697 A | 1/1992 | Manella | |
| 5,096,078 A * | 3/1992 | McQueeny | 215/231 |
| 5,096,822 A | 3/1992 | Rosenkrans, Jr. et al. | |
| 5,097,898 A | 3/1992 | Verkaart | |

| | | |
|---|---|---|
| 5,103,817 A * | 4/1992 | Reisdorf et al. ......... 128/207.15 |
| 5,106,373 A | 4/1992 | Augustine et al. |
| 5,108,372 A | 4/1992 | Swenson |
| 5,125,069 A | 6/1992 | O'Boyle |
| 5,125,900 A | 6/1992 | Teves |
| 5,129,033 A | 7/1992 | Ferrara et al. |
| 5,152,755 A | 10/1992 | Yoshinori |
| 5,169,389 A | 12/1992 | Kriesel |
| 5,180,896 A | 1/1993 | Gibby et al. |
| 5,184,613 A | 2/1993 | Mintz |
| 5,186,057 A | 2/1993 | Everhart |
| 5,195,976 A | 3/1993 | Swenson |
| 5,205,820 A | 4/1993 | Kriesel |
| 5,211,631 A | 5/1993 | Sheaff |
| 5,232,439 A | 8/1993 | Campbell et al. |
| 5,241,951 A | 9/1993 | Mason et al. |
| 5,243,833 A | 9/1993 | Coelho et al. |
| 5,245,693 A | 9/1993 | Ford et al. |
| 5,250,032 A | 10/1993 | Carter, Jr. et al. |
| 5,254,094 A | 10/1993 | Starkey et al. |
| 5,261,411 A | 11/1993 | Hughes |
| 5,261,875 A | 11/1993 | Spears et al. |
| 5,263,323 A | 11/1993 | Maus et al. |
| 5,263,929 A | 11/1993 | Falcone et al. |
| 5,269,749 A | 12/1993 | Koturov |
| 5,279,558 A | 1/1994 | Kriesel |
| 5,279,598 A | 1/1994 | Sheaff |
| 5,282,264 A | 1/1994 | Reeves et al. |
| 5,290,222 A | 3/1994 | Feng et al. |
| 5,290,230 A | 3/1994 | Ainsworth et al. |
| 5,297,234 A | 3/1994 | Harms et al. |
| 5,308,335 A | 5/1994 | Ross et al. |
| 5,318,540 A | 6/1994 | Athayde et al. |
| 5,330,431 A | 7/1994 | Herskowitz |
| 5,338,157 A | 8/1994 | Blomquist |
| 5,342,313 A | 8/1994 | Campbell et al. |
| 5,348,539 A | 9/1994 | Herskowitz |
| 5,364,371 A | 11/1994 | Kamen |
| 5,364,385 A | 11/1994 | Harms et al. |
| 5,370,674 A | 12/1994 | Farrell |
| 5,381,510 A | 1/1995 | Ford et al. |
| 5,389,078 A | 2/1995 | Zalesky et al. |
| 5,392,025 A | 2/1995 | Figh et al. |
| 5,397,875 A | 3/1995 | Bechtold, Jr. |
| 5,399,007 A | 3/1995 | Marconet |
| 5,399,166 A | 3/1995 | Laing |
| 5,408,576 A | 4/1995 | Bishop |
| 5,408,577 A | 4/1995 | Weber, Jr. et al. |
| 5,411,480 A | 5/1995 | Kriesel |
| 5,411,482 A | 5/1995 | Campbell |
| 5,417,274 A | 5/1995 | Verkaart |
| 5,420,962 A | 5/1995 | Bakke |
| 5,423,759 A | 6/1995 | Campbell |
| 5,433,704 A | 7/1995 | Ross et al. |
| 5,451,209 A | 9/1995 | Ainsworth et al. |
| 5,474,538 A | 12/1995 | Stihler et al. |
| 5,485,408 A | 1/1996 | Blomquist |
| 5,492,534 A | 2/1996 | Athayde et al. |
| 5,494,196 A * | 2/1996 | Tyner ......................... 222/147 |
| 5,512,043 A | 4/1996 | Verkaart |
| 5,514,095 A | 5/1996 | Brightbill et al. |
| 5,531,697 A | 7/1996 | Olsen et al. |
| 5,531,698 A | 7/1996 | Olsen |
| 5,538,399 A | 7/1996 | Johnson |
| 5,540,561 A | 7/1996 | Johnson |
| 5,564,915 A | 10/1996 | Johnson |
| 5,567,119 A | 10/1996 | Johnson |
| 5,567,136 A | 10/1996 | Johnson |
| 5,572,873 A | 11/1996 | Lavigne et al. |
| 5,573,516 A | 11/1996 | Tyner |
| 5,584,811 A | 12/1996 | Ross et al. |
| 5,590,648 A | 1/1997 | Mitchell et al. |
| 5,609,784 A | 3/1997 | Davenport |
| RE35,501 E | 5/1997 | Ross et al. |
| 5,647,854 A | 7/1997 | Olsen et al. |
| 5,649,910 A | 7/1997 | Kriesel et al. |
| 5,653,938 A | 8/1997 | Faries, Jr. et al. |
| 5,658,250 A | 8/1997 | Blomquist et al. |
| 5,658,252 A | 8/1997 | Johnson |
| 5,662,611 A | 9/1997 | Beiser et al. |
| 5,669,877 A | 9/1997 | Blomquist |
| 5,678,925 A | 10/1997 | Garmaise et al. |
| 5,681,284 A | 10/1997 | Herskowitz |
| 5,683,381 A | 11/1997 | Carr et al. |
| 5,690,614 A | 11/1997 | Carr et al. |
| 5,695,473 A | 12/1997 | Olsen |
| 5,707,151 A | 1/1998 | Parker et al. |
| 5,707,431 A | 1/1998 | Verkaart et al. |
| 5,713,864 A | 2/1998 | Verkaart |
| 5,720,728 A | 2/1998 | Ford |
| 5,729,653 A | 3/1998 | Magliochetti et al. |
| 5,733,263 A | 3/1998 | Wheatman |
| 5,738,442 A | 4/1998 | Paron et al. |
| 5,743,878 A | 4/1998 | Ross et al. |
| 5,744,806 A | 4/1998 | Frojd |
| 5,755,275 A | 5/1998 | Rose et al. |
| 5,772,409 A | 6/1998 | Johnson |
| 5,788,669 A | 8/1998 | Peterson |
| 5,788,671 A | 8/1998 | Johnson |
| 5,805,455 A | 9/1998 | Lipps |
| 5,806,528 A | 9/1998 | Magliochetti |
| 5,807,332 A | 9/1998 | Augustine et al. |
| 5,810,771 A | 9/1998 | Blomquist |
| 5,816,252 A | 10/1998 | Faries, Jr. et al. |
| 5,816,797 A | 10/1998 | Shoenfeld |
| 5,823,746 A | 10/1998 | Johnson |
| 5,824,000 A | 10/1998 | Pavlo et al. |
| 5,829,880 A | 11/1998 | Diedrich |
| 5,840,068 A | 11/1998 | Cartledge |
| 5,862,672 A | 1/1999 | Faries, Jr. et al. |
| 5,875,282 A | 2/1999 | Jordan |
| 5,876,370 A | 3/1999 | Blomquist |
| 5,879,143 A | 3/1999 | Cote et al. |
| 5,879,329 A | 3/1999 | Ginsburg |
| 5,879,621 A | 3/1999 | Faries, Jr. et al. |
| 5,891,096 A | 4/1999 | Hyun et al. |
| 5,893,843 A | 4/1999 | Rodrigues |
| 5,897,207 A | 4/1999 | Hartmann |
| 5,919,218 A | 7/1999 | Carr |
| 5,928,196 A | 7/1999 | Johnson et al. |
| 5,935,099 A | 8/1999 | Peterson et al. |
| 5,935,106 A | 8/1999 | Olsen |
| 5,954,485 A | 9/1999 | Johnson et al. |
| 5,961,492 A | 10/1999 | Kriesel et al. |
| 5,961,700 A | 10/1999 | Oliver |
| 5,961,866 A | 10/1999 | Hansen |
| 5,986,239 A | 11/1999 | Corrigan, III |
| 5,989,238 A | 11/1999 | Ginsburg |
| 5,997,927 A | 12/1999 | Gics |
| 6,024,539 A | 2/2000 | Blomquist |
| 6,035,102 A | 3/2000 | Bakke |
| 6,039,926 A | 3/2000 | Goldman |
| 6,045,648 A | 4/2000 | Palmgren et al. |
| 6,062,429 A | 5/2000 | West et al. |
| 6,096,007 A | 8/2000 | Haan et al. |
| 6,117,122 A | 9/2000 | Din et al. |
| 6,129,702 A | 10/2000 | Woias et al. |
| 6,139,528 A | 10/2000 | Kistner et al. |
| 6,142,974 A | 11/2000 | Kistner et al. |
| 6,146,359 A | 11/2000 | Carr et al. |
| 6,146,362 A | 11/2000 | Turnbull et al. |
| 6,158,458 A | 12/2000 | Ryan |
| 6,174,300 B1 | 1/2001 | Kriesel et al. |
| 6,175,688 B1 | 1/2001 | Cassidy et al. |
| 6,221,045 B1 | 4/2001 | Duchon et al. |
| 6,221,051 B1 | 4/2001 | Hjertman et al. |
| 6,236,809 B1 | 5/2001 | Cassidy et al. |
| 6,248,077 B1 | 6/2001 | Elson et al. |
| 6,254,572 B1 | 7/2001 | Knipfer et al. |
| 6,261,261 B1 | 7/2001 | Gordon |
| 6,264,049 B1 | 7/2001 | Shteynberg |
| 6,315,767 B1 * | 11/2001 | Dumont et al. ............... 604/404 |
| 6,316,750 B1 | 11/2001 | Levin |
| 6,334,707 B1 | 1/2002 | Ku |
| 6,344,033 B1 | 2/2002 | Jepson et al. |
| 6,467,953 B1 | 10/2002 | Faries, Jr. et al. |
| 6,480,257 B2 | 11/2002 | Cassidy et al. |
| 6,524,239 B1 | 2/2003 | Reed et al. |

| | | |
|---|---|---|
| 6,553,336 B1 | 4/2003 | Johnson et al. |
| 6,566,631 B2 | 5/2003 | Faries, Jr. et al. |
| 6,641,602 B2 | 11/2003 | Balding |
| 6,660,974 B2 | 12/2003 | Faries, Jr. et al. |
| 6,722,782 B2 | 4/2004 | Faries, Jr. et al. |
| 6,736,788 B1 | 5/2004 | Montgomery |
| 6,748,164 B1 | 6/2004 | Kuzyk |
| 6,768,085 B2 | 7/2004 | Faries, Jr. et al. |
| 6,788,885 B2 | 9/2004 | Mitsunaga et al. |
| 6,788,997 B1 | 9/2004 | Frederick |
| 6,810,881 B2 | 11/2004 | Faries, Jr. et al. |
| 6,824,528 B1 | 11/2004 | Faries, Jr. et al. |
| 6,850,252 B1 | 2/2005 | Hoffberg |
| 6,869,538 B2 | 3/2005 | Yu et al. |
| 6,910,485 B2 | 6/2005 | Faries, Jr. et al. |
| 6,967,575 B1 | 11/2005 | Dohrmann et al. |
| RE39,075 E | 4/2006 | Verkaart |
| 7,031,602 B2 | 4/2006 | Faries, Jr. et al. |
| 7,031,778 B2 | 4/2006 | Hsiung et al. |
| 7,041,941 B2 | 5/2006 | Faries, Jr. et al. |
| 7,090,658 B2 | 8/2006 | Faries, Jr. et al. |
| 7,176,030 B2 | 2/2007 | Faries, Jr. et al. |
| 7,262,698 B1 | 8/2007 | Frederick et al. |
| 7,307,245 B2 | 12/2007 | Faries, Jr. et al. |
| 7,326,882 B2 | 2/2008 | Faries, Jr. et al. |
| 7,417,205 B2 | 8/2008 | Faries, Jr. et al. |
| 7,540,864 B2 | 6/2009 | Faries, Jr. et al. |
| 7,608,460 B2 * | 10/2009 | Reed et al. .................. 436/163 |
| 7,611,504 B1 | 11/2009 | Faries, Jr. et al. |
| 7,726,876 B2 | 6/2010 | Laverdiere et al. |
| 7,740,611 B2 | 6/2010 | Faries, Jr. et al. |
| 7,942,821 B2 | 5/2011 | Umemura et al. |
| 7,942,851 B2 | 5/2011 | Faries, Jr. et al. |
| 8,226,293 B2 * | 7/2012 | Faries et al. ................... 374/138 |
| 8,226,605 B2 | 7/2012 | Faries, Jr. et al. |
| 8,313,462 B2 | 11/2012 | Faries, Jr. et al. |
| 2001/0009610 A1 | 7/2001 | Augustine et al. |
| 2002/0041621 A1 | 4/2002 | Faries, Jr. et al. |
| 2002/0081109 A1 | 6/2002 | Mitsunaga et al. |
| 2002/0156451 A1 | 10/2002 | Lenker |
| 2003/0000939 A1 | 1/2003 | Faries, Jr. et al. |
| 2003/0004470 A1 | 1/2003 | Hickerson et al. |
| 2003/0114795 A1 | 6/2003 | Faries, Jr. et al. |
| 2003/0216831 A1 | 11/2003 | Hart et al. |
| 2003/0222933 A1 | 12/2003 | Choi |
| 2003/0231990 A1 | 12/2003 | Faries, Jr. et al. |
| 2004/0170409 A1 | 9/2004 | Faries, Jr. et al. |
| 2004/0189258 A1 | 9/2004 | Lehmann et al. |
| 2004/0200480 A1 | 10/2004 | Faries, Jr. et al. |
| 2004/0200483 A1 | 10/2004 | Faries, Jr. et al. |
| 2004/0208780 A1 | 10/2004 | Faries, Jr. et al. |
| 2005/0059952 A1 * | 3/2005 | Giuliano et al. ............... 604/408 |
| 2005/0070845 A1 | 3/2005 | Faries, Jr. et al. |
| 2005/0142013 A1 | 6/2005 | Faries, Jr. et al. |
| 2005/0222933 A1 | 10/2005 | Wesby |
| 2005/0242930 A1 | 11/2005 | Nicolson et al. |
| 2006/0020255 A1 | 1/2006 | Cassidy et al. |
| 2006/0253075 A1 | 11/2006 | Faries, Jr. et al. |
| 2007/0000910 A1 | 1/2007 | Faries, Jr. et al. |
| 2007/0106243 A1 | 5/2007 | Faries, Jr. et al. |
| 2007/0142773 A1 | 6/2007 | Rosiello et al. |
| 2007/0161952 A1 | 7/2007 | Faries, Jr. et al. |
| 2007/0215018 A1 | 9/2007 | Faries, Jr. et al. |
| 2008/0021392 A1 * | 1/2008 | Lurvey et al. .................. 604/111 |
| 2008/0147016 A1 | 6/2008 | Faries et al. |
| 2008/0205481 A1 | 8/2008 | Faries et al. |
| 2010/0111135 A1 | 5/2010 | Faries, Jr. et al. |
| 2010/0168671 A1 | 7/2010 | Faries, Jr. et al. |
| 2010/0222762 A1 | 9/2010 | Faries, Jr. et al. |
| 2010/0222763 A1 | 9/2010 | Faries, Jr. et al. |
| 2012/0053518 A1 | 3/2012 | Faries, Jr. |
| 2012/0191050 A1 | 7/2012 | Faries, Jr. |

FOREIGN PATENT DOCUMENTS

| | | |
|---|---|---|
| FR | 2786057 | 5/2000 |
| GB | 2029677 A | 3/1980 |
| GB | 2336214 | 10/1999 |
| WO | 9221272 | 12/1992 |
| WO | 9320770 | 10/1993 |
| WO | 9838953 | 9/1998 |
| WO | 9845658 | 10/1998 |
| WO | 9922786 | 5/1999 |
| WO | 9926690 | 6/1999 |
| WO | 9958177 | 11/1999 |

OTHER PUBLICATIONS

"NAC PRN version: Needless Access Connector"; Porex Medical Products Group; retrieved from the Internet Mar. 6, 2002: www.porex.com/english/medical/mnac.asp; 1 page.

"Luer Lock Males"; Minerve Polymeres; retrieved from the Internet Feb. 6, 2002: http://minerve-polymeres.com/males.html; 2 pages.

"Luer Lock Femelles"; Minerve Polymeres; retrieved from the Internet Feb. 6, 2002: http://minerve-polymeres.com/femelles.html; 2 pages.

"HOTLINE Disposables"; retrieved from the Internet Feb. 4, 2002: www.simslevel1.com/hldsp.htm; 3 pages.

"I.V. Systems"; Life-Assist, Inc.; retrieved from the Internet Dec. 17, 2001; www.life-assist.com/iv/iv.html; 3 pages.

"HOTLINE Eliminates Patient Line Cool-Down"; retrieved from the Internet Jan. 18, 2002; www.simslevel1.com/hotln2.htm; 5 pages.

Health Devices, vol. 25, No. 10, Oct. 1996.

Minco Products, Inc., Bulletin CTI98, 1996.

Eurotherm Controls, Inc., Model 2116 Temperature Controller, 1997.

Ellenwood, Drop Detector, IBM Technical Bulletin, vol. 12, No. 5, Oct. 1969.

CBi Medical, Inc., IV Fluid Warmer Model 8362, 1992.

* cited by examiner

METHOD AND APPARATUS TO INDICATE PRIOR USE OF A MEDICAL ITEM

CROSS-REFERENCE TO RELATED APPLICATIONS

This application is a Divisional of U.S. patent application Ser. No. 11/581,795, entitled "Method and Apparatus to Indicate Prior Use of a Medical Item" and filed Oct. 17, 2006, which claims priority from U.S. Provisional Patent Application Ser. No. 60/730,361, entitled "Method and Apparatus to Indicate Prior Use of a Medical Item," and filed Oct. 27, 2005, the disclosure of which is incorporated herein by reference in its entirety.

BACKGROUND OF THE INVENTION

1. Technical Field

The present invention pertains to a device for use with a medical item that notifies a user of prior medical item use.

2. Discussion of Related Art

Generally, an intravenous (IV) fluid bag is shipped in a sealed plastic covering to protect the bag. The IV bag is generally in the form of a sealed plastic container and includes two ports. The ports may be utilized to connect the bag to an administration set to deliver IV fluid from the bag to a patient and to receive syringe needles for injection of medicaments into the IV fluid for infusion to a patient. The syringe needles pierce a penetrable seal on the injection port where the medicaments are injected before the needle is removed. The penetrable seal includes a self-sealing material to prevent leakage when a syringe needle is removed, where the sealing material is of sufficient strength to withstand numerous injections without a leak. Utilizing such injection ports enables introduction of medicaments without compromising the sterility of the bag.

When medical personnel administer IV fluid to a patient, it is important for the personnel to be aware of various characteristics of the fluid or infusion apparatus to avoid serious injury to the patient. For example, personnel awareness of prior use of or injection into an IV bag may prevent infusion of contaminated fluid or fluid with improper medication for a patient. Since the self-sealing material shows virtually no indication of a puncture, the IV bag does not provide any notification to medical personnel (e.g. nurse, pharmacist, etc.) of a prior injection of medication or a potentially dangerous substance. This may lead to an inadvertent injection of an improper combination of medications into the IV bag and/or infusion of dangerous substances into a patient, thereby causing significant patient injury.

There is therefore a need to develop an indicator of prior use of a medical item capable of informing medical personnel of the possibility that a medication has been added to an IV bag. More specifically, there is a need to develop a system of visually alerting medical personnel of a prior use of an IV bag injection port.

SUMMARY OF THE INVENTION

Accordingly, the present invention monitors an IV bag injection port and informs the user of prior injections. The present invention employs an object and/or a sealed chamber within a transparent IV fluid bag injection port. In the case of the object, notification of prior use is achieved when the object's appearance within the injection port is altered. With respect to the sealed chamber, the chamber's seal is breached to allow fluid to pass between the chamber and the IV bag to change the appearance of the contents of the chamber. Because the injection port walls are at least partially transparent, medical personnel are able to observe the altered appearance of either the object or the sealed chamber within the injection port.

An embodiment of the present invention may include positioning an object within the injection passageway of an injection port. The proximal end of the port includes a penetrable, resealable membrane. Within the port, the object is sized and/or positioned so that the needle must pass through the membrane and the object in order to discharge syringe fluid into the IV bag. The needle contacts the object to alter the object's appearance.

Alternative embodiments may be implemented in various manners. For example, a sealed chamber may be defined between the membrane and a fluid barrier isolating the chamber from fluid in the IV bag. The sealed chamber itself or an object disposed therein changes appearance to indicate prior use. With this arrangement, in order to introduce syringe fluid into the IV bag, the needle must pass through the membrane and chamber before breaching the fluid barrier. The visual notification of prior use occurs within the sealed chamber when either the needle alters the object's appearance, the object contacts fluid flowing from the IV bag through the breached fluid barrier into the chamber thereby changing the object's appearance, or fluid from the IV bag is present within the chamber.

Any object that is susceptible to a change in appearance when contacted by a needle may be utilized. For example, the object can be a device that is inflated within the passage of the injection port such that a needle passing through the injection port must pass through the inflated object, thereby deflating the object. The deflated object has a significantly different appearance than the inflated object. In any case, the mode of altering the object's appearance need not be inflation/deflation. Any other mode may be employed that utilizes contact between the object and the needle as it passes through the injection port passageway. For example, the object's appearance may be altered by pivoting the object within the injection port, where the syringe needle could provide the pivot force to pivot the object.

Further, a reactive material may be placed in the sealed chamber. The reactive material reacts by changing appearance upon contacting IV fluid. When pierced, the fluid barrier allows IV bag fluid to flow into the previously sealed chamber to interact with the reactive material to alter the appearance of that material. For example, the reactive material may change color or shape, or may dissolve when placed in contact with IV fluid. The altered appearance of the reactive material in the chamber notifies a user of a prior injection. A reactive material may be chosen to react with a particular substance. In other words, the reactive material may be utilized to specifically verify the presence of a particular substance in the IV bag.

Moreover, the sealed chamber may include an alert fluid. The fluid barrier separates the sealed chamber from the fluid in the IV bag. In this case, the visual alert is provided when the needle pierces the fluid barrier to allow the alert fluid to flow from the sealed chamber into to the IV bag. The visual alert can be amplified by providing a colored alert fluid (different from the color of the IV fluid) in the sealed chamber. In other words, the presence of the alert or colored fluid within the IV bag notifies medical personnel that the IV bag has received a prior injection.

In addition, the sealed chamber may be employed without an object. In this case, the visual alert is provided by the needle piercing the fluid barrier to allow fluid to flow from the IV bag into the sealed chamber. The presence of fluid within the sealed chamber notifies medical personnel that the IV bag has received a prior injection.

The above and still further features and advantages of the present invention will become apparent upon consideration of the following detailed description of specific embodiments thereof, particularly when taken in conjunction with the accompanying drawings wherein like reference numerals in the various figures are utilized to designate like components.

DETAILED DESCRIPTION OF THE PREFERRED EMBODIMENTS

Figure 1:
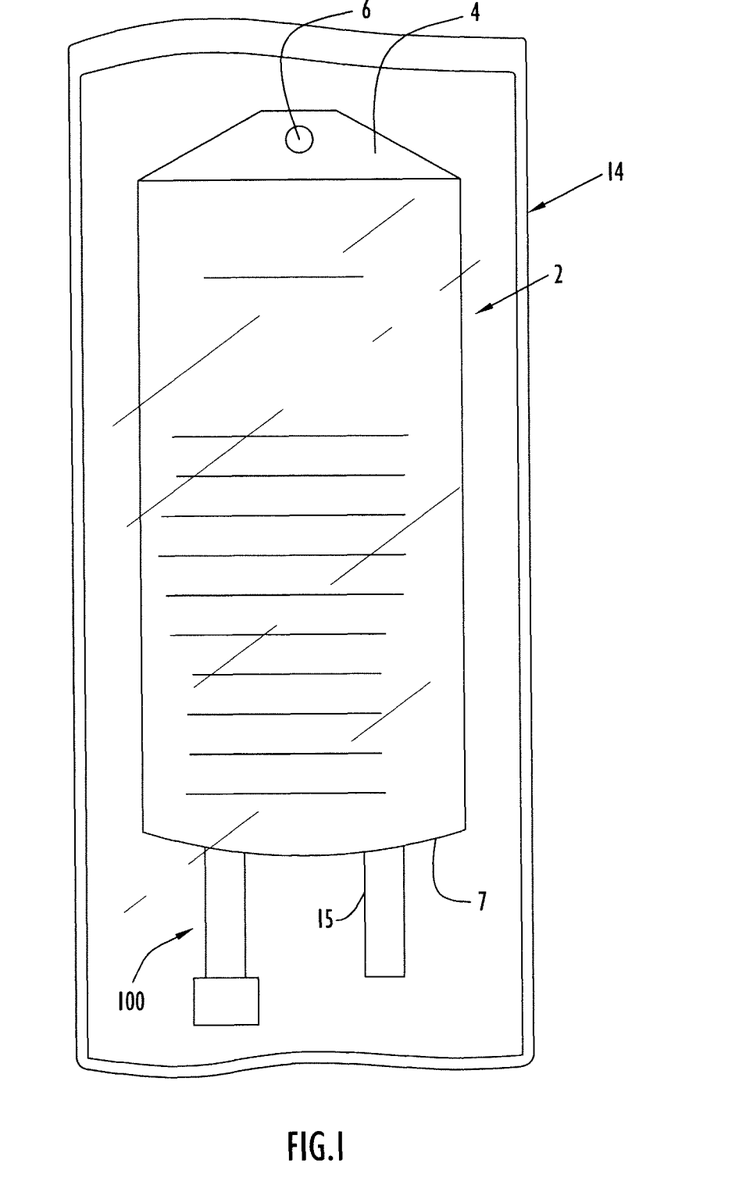
FIG. 1 is a front view in elevation of an exemplary IV bag enclosed in a transparent packaging material and including an injection port that indicates a prior injection according to the present invention.

An exemplary IV bag including an injection port that indicates a prior injection according to the present invention is illustrated in FIG. 1. Specifically, IV bag 2 is enclosed in a transparent package covering 14, preferably utilized during shipping to protect the bag. IV bag 2 includes a tab 4 at a bag upper end with an aperture 6 for hanging or suspending the bag from a structure (e.g., an IV pole, etc.). Bag 2 further includes a discharge port 15 and an injection port 100 each connected to a bottom bag area 7. Discharge port 15 directs fluid from IV bag 2 to a patient, while injection port 100 enables injection of substances into IV bag 2 and notifies medical personnel of prior injections as described below.

Figure 2:
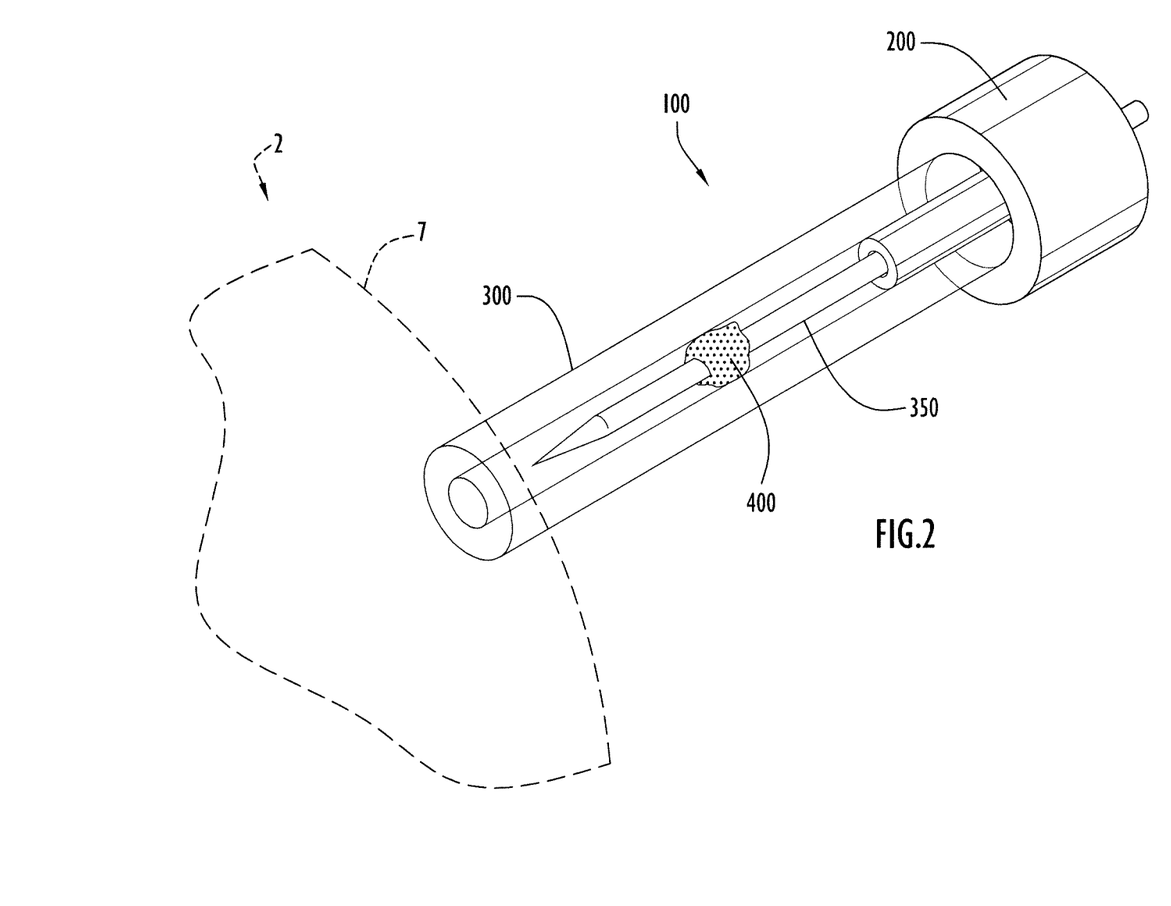
FIG. 2 is a perspective view of an injection port of the IV bag of FIG. 1 including an inflatable balloon to indicate injection port usage according to the present invention.

Injection port 100 according to the present invention is illustrated in FIG. 2. Specifically, injection port 100 includes a seal element 200, a needle port 300, and a balloon 400. Seal element 200 is disposed at an injection port proximal end and receives a syringe needle 350. Needle port 300 is connected to the distal end of seal element 200 and extends for attachment to IV bag area 7. Balloon 400 is disposed within an intermediate portion of needle port 300, preferably in an inflated state, and is filled with the same or substantially similar IV fluid contained in the bag or other fluid harmless to the patient. When needle 350 is inserted into seal element 200, the needle extends into and through needle port 300, thereby puncturing balloon 400. Balloon 400 is visible to medical personnel, where a deflated balloon status indicates a prior injection.

Figure 3:
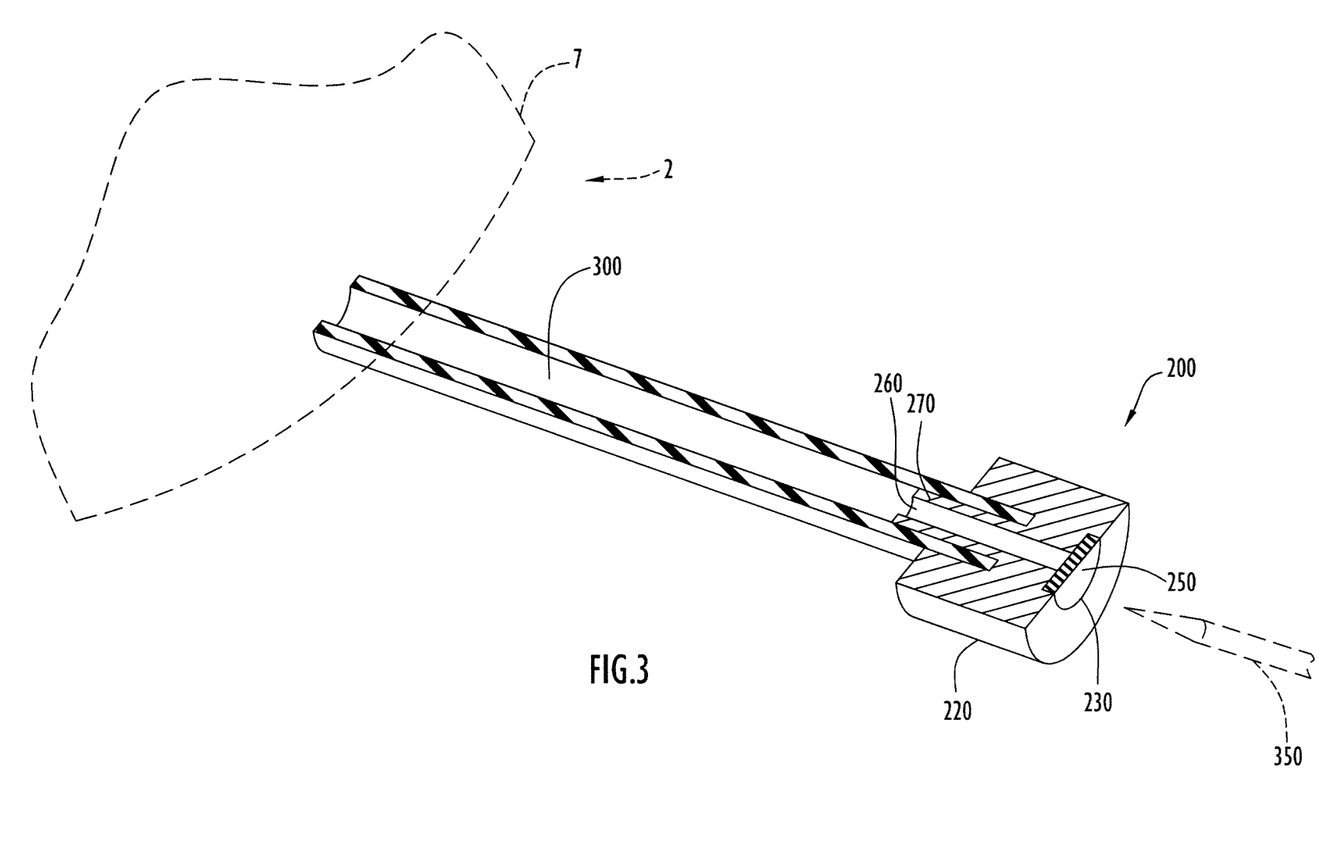
FIG. 3 is a view in perspective and partial section of the seal element of the injection port of FIG. 2.

Referring to FIG. 3, seal element 200 includes a cap 220 and a projection 270. Cap 220 is generally annular and includes a central opening or passage 230 defined therethrough. The opening includes transverse cross-sectional dimensions greater than those of a syringe or other needle 350 and less than those of needle port 300. The proximal end of passage 230 is covered by a penetrable, resealable membrane 250. The membrane is preferably constructed of a conventional self-sealing material to prevent leakage in response to withdrawal of needle 350 from injection port 100. The material is typically of sufficient strength to withstand several injections without a leak.

Projection 270 is substantially cylindrical and extends from the distal end of passage 230. The projection includes a channel 260 defined therethrough and transverse cross-sectional dimensions substantially similar to those of passage 230. Needle port 300 is disposed over projection 270 and is attached to the distal end of cap 220. The needle port may be attached to the projection outer surface and/or cap 220 via any conventional techniques (e.g., heat welding, heat sealing, adhesives, RF heating, etc.). The channel and cap passage enable syringe or other needle 350 to traverse seal element 200 for injection of medication into bag 2.

Figure 4:
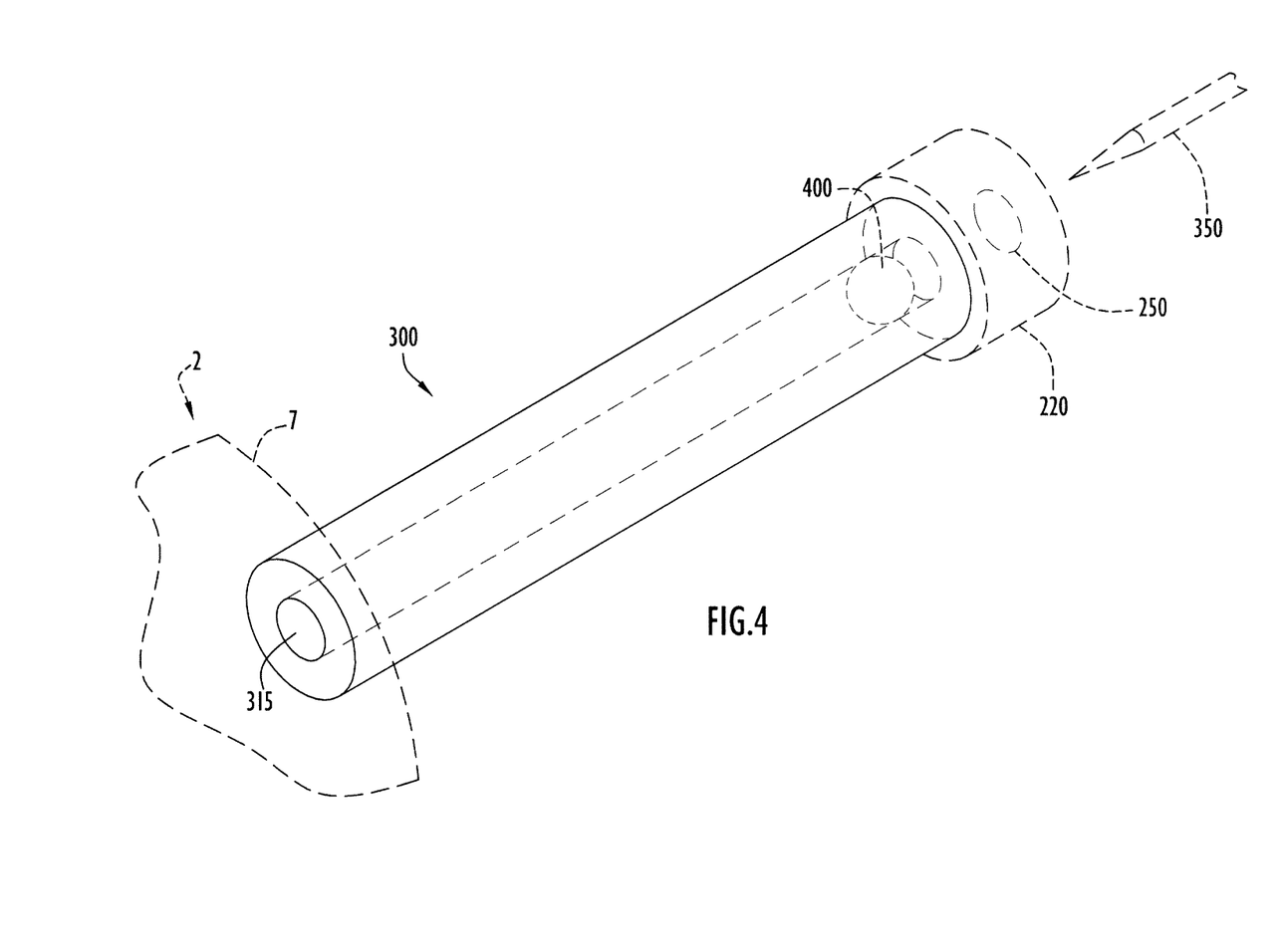
FIG. 4 is a perspective view of the section of the injection port of FIG. 2 housing the inflatable balloon according to the present invention.

Needle port 300 is illustrated in FIG. 4. Specifically, needle port 300 is preferably in the form of a generally cylindrical and transparent tubular member with a tube passage 315 defined therethrough. The transverse cross-sectional dimensions of tube passage 315 is slightly greater than those of projection 270 (FIG. 3) to enable projection 270 to be received within a proximal portion of that passage as described above. The distal end of needle port 300 is attached to bag area 7 of IV bag 2. Needle port tube passage 315 is in fluid communication with IV bag 2, thereby enabling substances injected via the injection port to enter and mix with the IV fluid.

Since conventional injection ports merely include a self-sealing material, there is virtually no mechanism for recording the occurrence of a prior injection into an IV bag. Thus, medical personnel (e.g., a nurse, a pharmacist, etc.) may inadvertently provide IV bags with improper medication or other substances, or a contaminated IV bag may be inadvertently utilized, thereby risking injury to a patient as described above. The present invention employs an indicator within the injection port to indicate the occurrence of an injection to medical personnel.

In particular, needle port 300 includes a balloon 400 or other inflatable or enlarged object to indicate the occurrence of a prior injection. Balloon 400 is manufactured within needle port 300 and is preferably filled with air, substantially the same fluid within IV bag 2, or another harmless substance. Balloon 400 is preferably disposed at the needle port proximal end to enable at least a minimal degree of insertion of needle 350 within the needle port to contact the balloon and indicate a prior injection. In other words, this enables the balloon to indicate prior full or partial insertions of syringe or other needles into the needle port. Partial (or full) needle insertions may occur due to tampering or inadvertent use by medical personnel. However, the balloon may be disposed at any suitable location within the needle port enabling or requiring contact with inserted needle 350 and visibility of the balloon to medical personnel. Balloon 400 is typically secured to the needle port interior surface via conventional techniques (e.g., heat welding, heat sealing, adhesives, RF heating, etc.) and may seal the fluid passageway against fluid flow. When a needle is inserted through membrane 250, the needle enters needle port 300. Since balloon 400 is disposed proximate cap 220, the needle ruptures the balloon. The fluid contained by balloon 400 is released and the balloon enters a deflated state indicating the occurrence of the injection.

Medical personnel view the deflated state of balloon 400 and are informed of a prior injection (e.g., or any tampering or inadvertent use due to a needle insertion). Thus, medical personnel (e.g., nurse, pharmacist, etc.) receiving an IV bag 2 according to the present invention may view the state of balloon 400 to determine the occurrence of prior injections or a compromised state of IV bag 2 prior to use.

Balloon 400 may be inflated and/or be secured to the needle port interior surfaces to form a seal and completely block fluid flow through needle port 300. Since fluid cannot pass balloon 400, fluid from needle 350 cannot enter the IV bag without the needle piercing balloon 400. In other words, an inflated balloon 400 indicates that no syringe fluid has entered IV bag 2. When a needle is inserted through membrane 250 and enters needle port 300, the needle pierces balloon 400 and discharges syringe fluid into the IV bag fluid.

Different types of objects may be utilized in needle port 300 that alter appearance to indicate the occurrence of an injection. The objects may be ruptured, reoriented, deformed, change color, dissolve, swell or provide any other manner of visually alerting a user that an injection has occurred. The objects need only be arranged such that breach of the access to the IV bag fluid results in an altered appearance of the chosen object.

Figure 5:
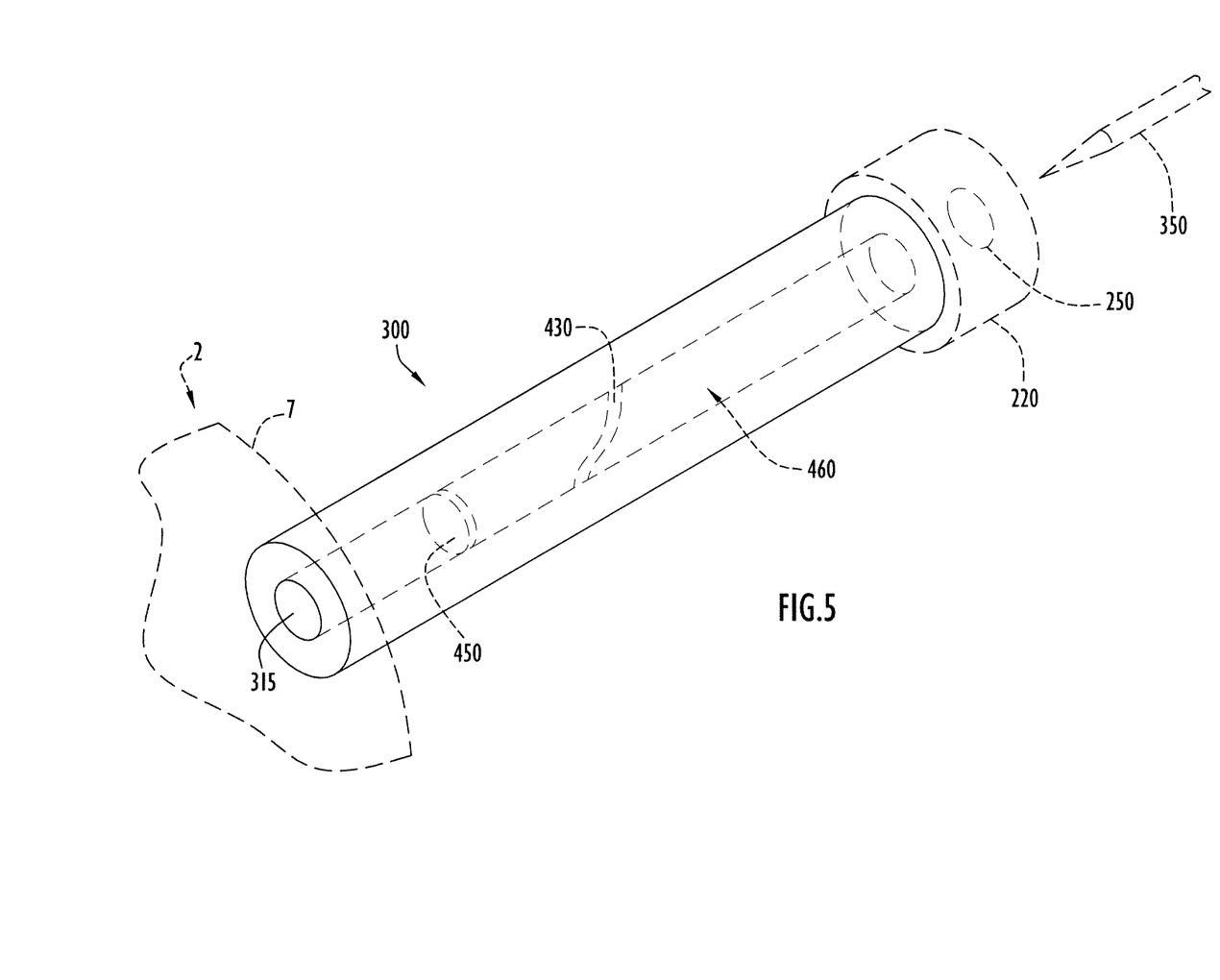
FIG. 5 is a perspective view of an alternative embodiment of an injection port including reactive paper or other material that changes color to indicate an injection according to the present invention.

Referring to FIG. 5, a sealed chamber 460 may be defined within needle port 300 between cap 220 and a fluid barrier or membrane 450. A needle 350 must pierce membrane 250 and penetrate fluid barrier 450 in order to introduce medication or other fluid into IV bag 2. Fluid entering or leaving the breached chamber creates an informative difference in appearance. For example, a chemically sensitive paper or other substrate may be disposed within sealed chamber 460 in needle port 300 to indicate the occurrence of an injection. Initially, needle port 300 is substantially similar to the needle port described above and includes a chemically sensitive paper or other material 430 within sealed chamber 460. Paper/material 430 is preferably dyed and reacts to fluid exposure by changing color. Basically, paper/material 430 measures alkalinity of the fluid, where paper/material 430 changes color in accordance with the alkalinity of the fluid contacting the paper. Paper/material 430 may be implemented by any conventional or other chemical sensing strips (e.g., pH paper, etc.) altering appearance to indicate results. Paper/material 430 is preferably secured toward an interior surface of tube passage 315 to avoid interfering with a needle 350 inserted into the injection port.

Fluid barrier 450 is disposed within tube passage 315 distally of paper 430 and includes dimensions sufficient to isolate paper 430 from fluid within IV bag 2. Preferably, fluid barrier 450 is disposed toward the needle port proximal end as described above to be ruptured by needle 350 in response to at least a minimal degree of needle insertion within the needle port. Partial (or full) needle insertions may occur due to tampering or inadvertent use by medical personnel. However, fluid barrier 450 may be implemented by any suitable materials and may be disposed at any suitable location to isolate paper 430 and be contacted by an inserted needle 350. When a needle is inserted through membrane 250 and enters needle port 300, the needle pierces fluid barrier 450, thereby causing fluid from IV bag 2 to flow into chamber 460 and contact paper/material 430. Paper/material 430 changes color to indicate the occurrence of the injection (e.g., or any tampering or inadvertent use due to a needle insertion) and is visible through transparent needle port 300.

In addition, a syringe needle may be partially inserted into sealed chamber 460 without piercing fluid barrier 450 to dispense fluid from the syringe. This may occur due to tampering or inadvertent use by medical personnel. In this case, the dispensed fluid contacts paper/material 430 that changes color to indicate the occurrence of the tampering or injection.

Figure 6:
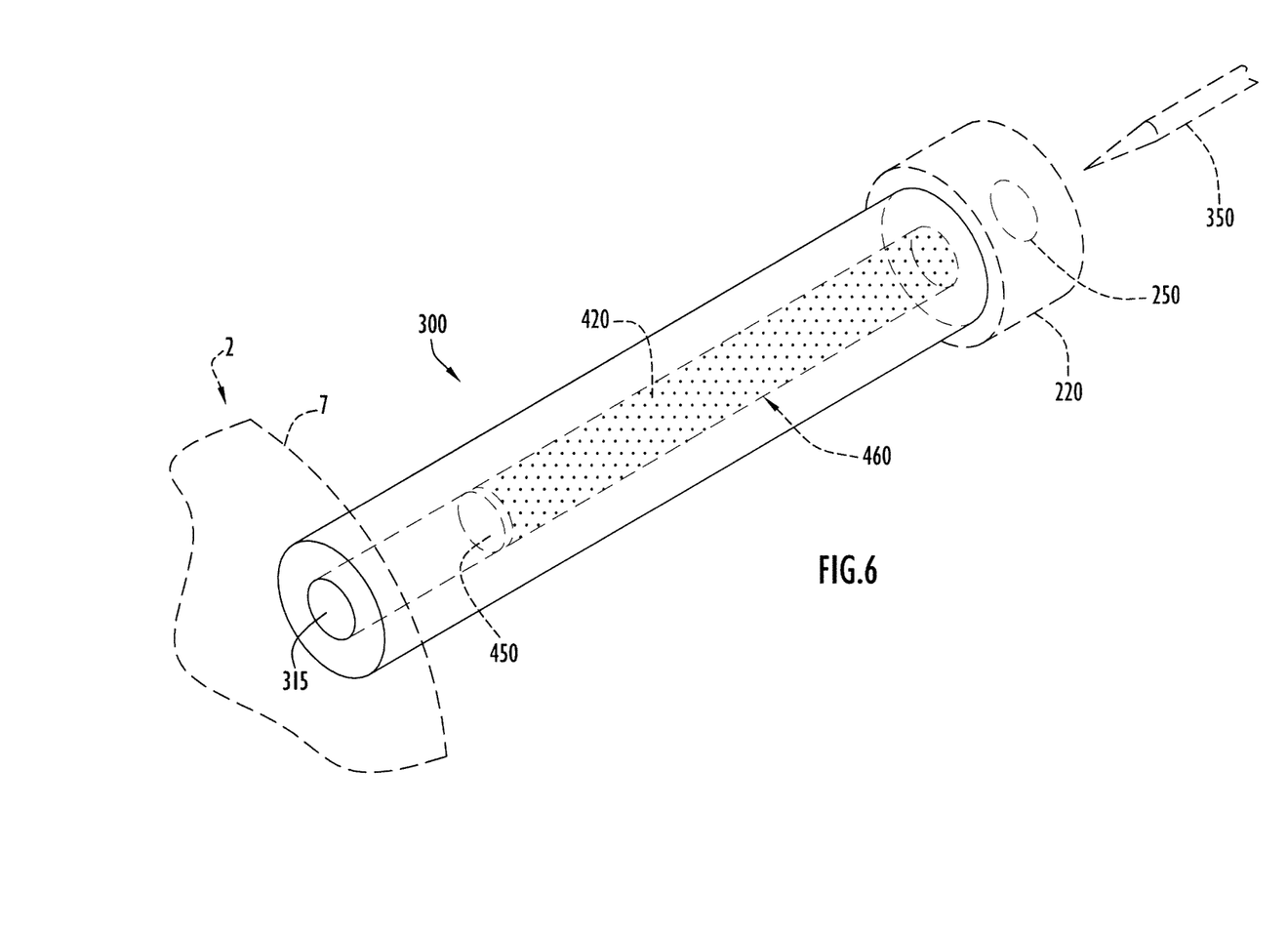
FIG. 6 is a perspective view of yet another embodiment of an injection port including colored fluid to indicate an injection according to the present invention.

Further, a colored fluid may be utilized in sealed chamber 460 to indicate the occurrence of an injection as illustrated in FIG. 6. Initially, needle port 300 is substantially similar to the needle port described above and includes sealed chamber 460 with fluid barrier 450. The sealed chamber further includes a sterile colored fluid 420 (e.g., fluid that will not cause injury to the patient). Fluid 420 is substantially similar to the fluid within IV bag 2 and may include any suitable additives to attain any desired color or other characteristic visually distinguishable from the fluid within IV bag 2. Fluid barrier 450 is disposed in tube passage 315 of needle port 300 distally of fluid 420 and includes dimensions sufficient to isolate colored fluid 420 from the fluid within IV bag 2. Preferably, fluid barrier 450 is disposed toward the needle port proximal end as described above to be ruptured by needle 350 in response to at least a minimal degree of needle insertion within the needle port. Partial (or full) needle insertions may occur due to tampering or inadvertent use by medical personnel. However, the fluid barrier may be disposed at any suitable location to enable or require contact by an inserted needle 350.

When needle 350 is inserted through membrane 250 and enters needle port 300, the needle pierces fluid barrier 450, thereby causing colored fluid 420 to flow out of sealed chamber 460 and into IV bag 2. The fluid in IV bag 2 changes color indicating the occurrence of the injection (e.g., or any tampering or inadvertent use due to a needle insertion). Alternatively, the colored fluid may be placed within a container, such as balloon 400, that is disposed in needle port 300. Preferably, the container is disposed at the needle port proximal end as described above to be ruptured by needle 350 in response to at least a minimal degree of needle insertion within the needle port. Partial (or full) needle insertions may occur due to tampering or inadvertent use by medical personnel. In this case, when the balloon is ruptured by the needle, the colored fluid is released and indicates occurrence of the injection (e.g., or any tampering or inadvertent use due to a needle insertion).

Figure 7:
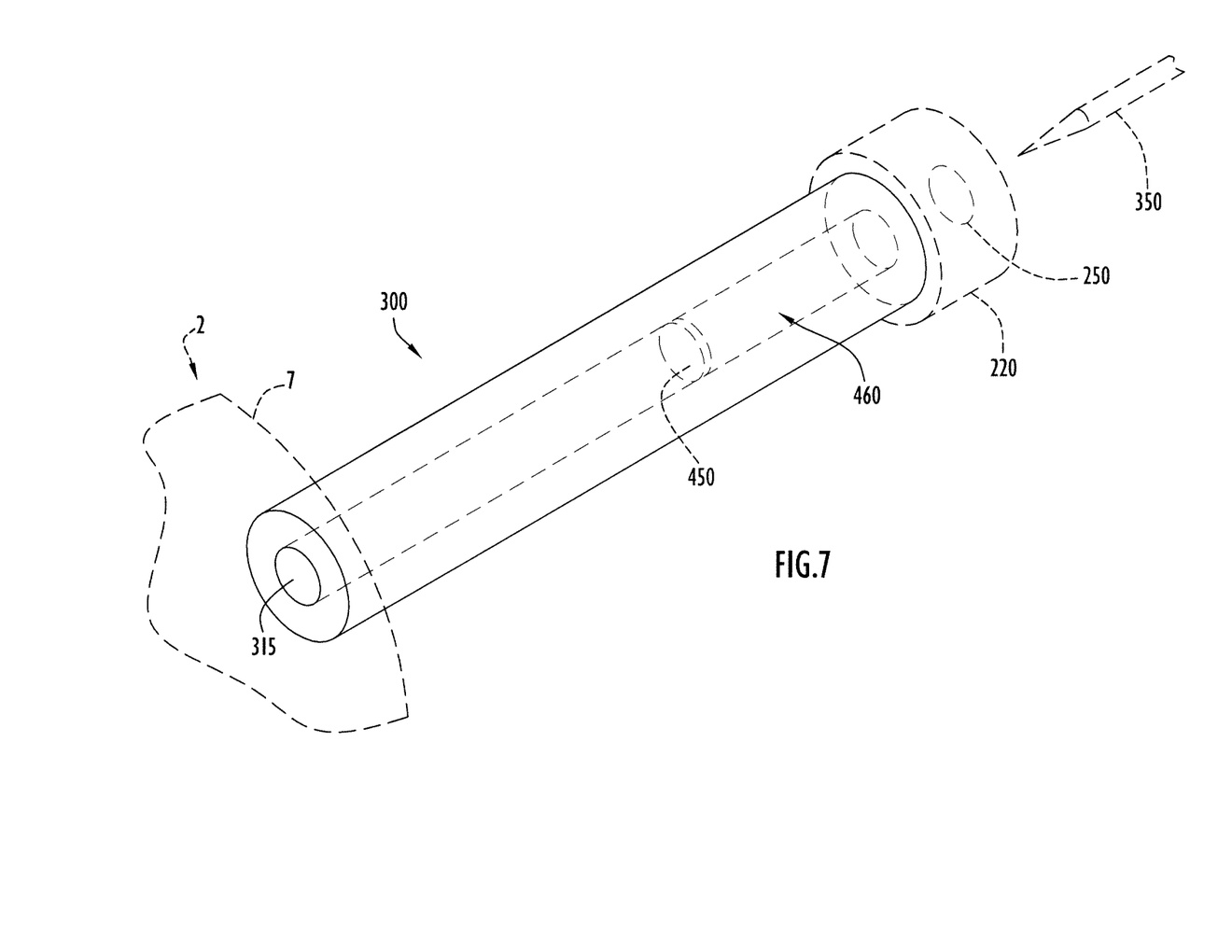
FIG. 7 is a perspective view of still another embodiment of an injection port including a sealed chamber to indicate an injection according to the present invention.

In addition, an empty sealed chamber 460 may be utilized to indicate the occurrence of an injection as illustrated in FIG. 7. Initially, needle port 300 is substantially similar to the needle port described above and includes sealed chamber 460 with fluid barrier 450. When a needle 350 is inserted through membrane 250 and enters needle port 300, the needle pierces fluid barrier 450, thereby causing fluid from IV bag 2 to flow into chamber 460. The presence of fluid in the chamber indicates the occurrence of the injection.

In addition, a syringe needle may be inserted into sealed chamber 460 without piercing fluid barrier 450 to dispense fluid from the syringe. This may occur due to tampering or inadvertent use of medical personnel. In this case, the presence of dispensed fluid in the chamber indicates the occurrence of the tampering or injection.

Operation of the present invention is described with reference to FIGS. 1-7. Initially, a patient is to be treated using IV bag 2 with an IV administration set. IV bag 2 includes injection port 100 for introducing medicine into the IV bag 2 via a syringe needle 350, and discharge port 15 to enable fluid to flow to the patient. Medical personnel check object 400 or chamber 460 within needle port 300, and/or the IV fluid for an indication of prior injections as described above. If an injection occurred, IV bag 2 is compromised and a new uncompromised IV bag 2 is selected for use. Once a satisfactory bag is selected, discharge port 15 is coupled to the administration set for infusion into the patient. Prior to or during infusion, medication may need to be introduced into the IV fluid. Accordingly, medical personnel insert a syringe or other needle 350 into injection port 100 via membrane 250. The needle enters needle port 300 and pierces balloon 400 (FIG. 1). The balloon subsequently deflates to indicate occurrence of the injection. Alternatively, injection port 100 may include a sealed chamber 460 (FIGS. 5-7), where the chamber includes paper or other material 430 (FIG. 5) or colored fluid 420 (FIG. 6). In this case, the needle is inserted into needle port 300 and pierces fluid barrier 450 to expose the paper/material to fluid from IV bag 2 (FIG. 5), to enable colored fluid 420 to enter the IV bag (FIG. 6) or to enable fluid from the IV bag to enter the sealed chamber (FIG. 7). The paper/material and IV fluid undergo a color change, whereas the sealed chamber receives fluid from IV bag 2, to indicate the occurrence of the injection as described above.

It will be appreciated that the embodiments described above and illustrated in drawings represent only a few of the many ways of implementing a method and apparatus to indicate prior use of a medical item.

The IV bag may be of any shape or size, may be constructed of any suitable materials and may include any quantity of discharge, injection or other ports disposed at any suitable locations. The present invention may be utilized with any medical or other items (e.g., IV lines or connectors, solution containers, etc.) to indicate insertion of various fluids or substances. The injection port may be of any quantity, shape or size, may be constructed of any suitable materials (e.g., plastic, etc.) and may be disposed at any suitable locations. The injection port may be formed from a single piece, an integral unit or separate components (e.g., cap, needle port, etc.). The injection port may be attached to the IV bag via any conventional or other techniques (e.g., heat welding, heat sealing, screw thread, snap fit, RF heating, etc.).

The seal element may be of any quantity, shape or size and may be constructed of any suitable materials (e.g., plastic, etc.). The seal element may be formed from a single piece, an integral unit or separate components (e.g., cap, projection, etc.) and may be attached to the needle port via any conventional or other techniques (e.g., heat welding, heat sealing, RF heating, etc.). The membrane may be of any quantity, shape or size, may be disposed at any suitable locations and may be constructed of any suitable self-sealing or other materials preventing leaks.

The needle port may be of any quantity, shape or size and may be constructed of any suitable materials (e.g., materials for IV lines or tubes, plastic, etc.). The needle port may be transparent or translucent, or include sufficient transparent and/or translucent sections for visibility of the balloon, fluid or other object. The needle port may include any suitable object that alters appearance and/or position in response to contact with the fluid and/or needle (e.g., balloon, color changing material or fluid, deformable object, etc.).

The object may be of any quantity and disposed at any suitable location within the needle port. The colored fluid employed may be of any desired amount and may be of any suitable color distinguishable from the IV bag or application fluid. The reactive paper or material may be of any quantity, shape or size, and may be implemented by any material that may react or change characteristics (e.g., dissolve, change to any desired color or colors (e.g., preferably those that are easily visible or distinguishable from the needle port), change shape or size, etc.) in response to any suitable properties of the fluid (e.g., alkalinity, pH, temperature, etc.). The reactive paper may be configured to indicate the presence of any specific chemical, substance or type of fluid.

The sealed chamber may be of any quantity, shape or size, may be disposed at any suitable locations and may include any objects to indicate the occurrence of an injection, such as the objects described above.

The fluid barrier may be of any quantity, shape or size, may be disposed at any suitable locations isolating the object and/or chamber from the fluid and may be constructed of any suitable materials (e.g., plastic, etc.). The fluid barrier may alternatively be a rigid object that may be displaced or include displaceable sections in response to contact with the needle.

The injection port may be configured for use with any suitable instruments inserting medication or other substances or fluids into the IV bag. Further, the injection port may be utilized with any equipment utilizing injection ports or enabling introduction of medication or other substances or fluids (e.g., IV bags, IV administration sets, etc.).

The present invention may utilize plural indicators, where the alert mechanisms of present invention embodiments may be used individually or in any combination (e.g., a reactive material may be disposed within a sealed chamber with a deflatable object, colored fluid may be utilized in combination with the deflatable object, etc.).

The present invention is not limited to the applications described above, but may be utilized to notify a user of prior use or a compromised state of any medical or other item (e.g., IV line or connector, solution container, etc.). For example, the present invention may be utilized for any application where user notification is desired in response to an attempt to introduce a substance into an environment of concern.

From the foregoing description, it will be appreciated that the invention makes available a novel method and apparatus to indicate prior use of a medical item, wherein an object and/or a sealed chamber within an IV fluid bag injection port is employed to visually notify a user of prior use.

Having described preferred embodiments of a new and improved method and apparatus to indicate prior use of a medical item, it is believed that other modifications, variations and changes will be suggested to those skilled in the art in view of the teachings set forth herein. It is therefore to be understood that all such variations, modifications and changes are believed to fall within the scope of the present invention as defined by the appended claims.

What is claimed is:

1. A method of notifying a user of a prior injection within a medical item including a receptacle containing a medical fluid, wherein said medical item includes a port to receive an injection of a medical substance for said medical item, wherein said port includes a membrane penetrable by an instrument, a tubular member extending from said membrane with a passage defined therethrough for fluid communication with said receptacle and to receive said instrument within said passage for said injection, and an indicator disposed within said passage and triggered by direct contact with said instrument, said method comprising:

(a) determining occurrence of said instrument penetrating said membrane and traversing said passage for said injection of said substance into said medical item and altering an appearance of at least one of said indicator disposed within said passage and said medical fluid to indicate said occurrence of said injection in response to said instrument triggering said indicator by traversing said passage and directly contacting said indicator during said injection.

2. The method of claim 1, wherein said indicator includes an inflatable device, and step (a) further includes:

(a.1) transitioning said inflatable device between inflated and deflated states in response to said instrument traversing said passage to indicate said occurrence of said injection.

3. A method of notifying a user of prior use of a medical item containing a medical fluid, wherein said medical item includes a port with a passage to enable insertion of a substance into said medical item via an instrument, said method comprising:
  (a) determining use of said medical item and altering an appearance of at least one of an indicator disposed within said passage and said medical fluid in response to said insertion of said instrument within said passage, wherein said indicator includes an inflatable device that is filled with a colored fluid, and step (a) further includes:
    (a.1) altering an appearance of said medical fluid via said colored fluid to indicate said medical item use in response to said instrument piercing said inflatable device during said insertion within said passage.

4. The method of claim 1, wherein said indicator includes a chamber defined within said passage by a fluid barrier that isolates said chamber from said medical fluid, and wherein said chamber includes an object and step (a) further includes:
  (a.1) altering an appearance of at least one of said object and said medical fluid in response to said instrument traversing said passage to indicate said occurrence of said injection.

5. A method of notifying a user of prior use of a medical item containing a medical fluid, wherein said medical item includes a port with a passage to enable insertion of a substance into said medical item via an instrument, said method comprising:
  (a) determining use of said medical item and altering an appearance of at least one of an indicator disposed within said passage and said medical fluid in response to said insertion of said instrument within said passage, wherein said indicator includes a chamber defined within said passage by a fluid barrier that isolates said chamber from said medical fluid, and wherein said chamber includes an object and step (a) further includes:
    (a.1) altering an appearance of at least one of said object and said medical fluid in response to said insertion of said instrument within said passage to indicate said medical item use, wherein said object includes a reactive material that changes a material characteristic in response to contact with said medical fluid, and step (a.1) further includes:
      (a.1.1) altering said material characteristic to indicate said medical item use by enabling said medical fluid to contact said reactive material in response to said instrument piercing said fluid barrier during said insertion within said passage.

6. The method of claim 5, wherein said reactive material changes color in response to contact with said medical fluid, and step (a.1.1) further includes:
  (a.1.1.1) changing said reactive material color to indicate said medical item use by enabling said medical fluid to contact said reactive material.

7. A method of notifying a user of prior use of a medical item containing a medical fluid, wherein said medical item includes a port with a passage to enable insertion of a substance into said medical item via an instrument, said method comprising:
  (a) determining use of said medical item and altering an appearance of at least one of an indicator disposed within said passage and said medical fluid in response to said insertion of said instrument within said passage, wherein said indicator includes a chamber defined within said passage by a fluid barrier that isolates said chamber from said medical fluid, and wherein said chamber includes an object and step (a) further includes:
    (a.1) altering an appearance of at least one of said object and said medical fluid in response to said insertion of said instrument within said passage to indicate said medical item use, wherein said object includes a colored fluid, and step (a.1) includes:
      (a.1.1) altering said appearance of said medical fluid by said colored fluid to indicate said medical item use in response to said instrument piercing said fluid barrier during said insertion within said passage.

8. The method of claim 1, wherein said indicator includes a chamber defined within said passage by a fluid barrier that isolates said chamber from said medical fluid, and step (a) further includes:
  (a.1) enabling said medical fluid to flow within said chamber to indicate said occurrence of said injection in response to said instrument piercing said fluid barrier during traversal of said passage.

9. The method of claim 1, wherein said medical item includes a medical solution container.

10. The method of claim 1, wherein said medical item includes an intravenous solution bag, said port includes an injection port and said instrument includes a needle.

* * * * *